US008153587B2

(12) United States Patent
Ault et al.

(10) Patent No.: US 8,153,587 B2
(45) Date of Patent: *Apr. 10, 2012

(54) ORALLY ADMINISTERING PARATHYROID HORMONE AND CALCITONIN

(75) Inventors: Joseph M Ault, Blairstown, NJ (US); Moise Azria, Basel (CH); Simon D Bateman, Randolph, NJ (US); James F McLeod, Morristown, NJ (US)

(73) Assignee: Novartis AG, Basel (CH)

( * ) Notice: Subject to any disclaimer, the term of this patent is extended or adjusted under 35 U.S.C. 154(b) by 53 days.

This patent is subject to a terminal disclaimer.

(21) Appl. No.: 12/020,700

(22) Filed: Jan. 28, 2008

(65) Prior Publication Data

US 2008/0119411 A1    May 22, 2008

Related U.S. Application Data

(63) Continuation of application No. 10/478,631, filed as application No. PCT/EP02/06017 on May 31, 2002, now abandoned.

(60) Provisional application No. 60/295,169, filed on Jun. 1, 2001.

(51) Int. Cl.
*A61K 38/29* (2006.01)
*A61K 38/23* (2006.01)
*A61P 5/18* (2006.01)
*C07K 14/635* (2006.01)
*C07K 14/585* (2006.01)

(52) U.S. Cl. ..................... 514/11.8; 514/11.9
(58) Field of Classification Search .......... 514/12, 514/11.8, 11.9; 424/491
See application file for complete search history.

(56) References Cited

U.S. PATENT DOCUMENTS

| 4,692,433 | A | * | 9/1987 | Hostetler et al. | ............... | 514/12 |
| 5,364,840 | A | | 11/1994 | Basava et al. | | |
| 5,620,708 | A | | 4/1997 | Amkraut et al. | ............... | 424/491 |
| 5,866,536 | A | * | 2/1999 | Leone-Bay et al. | ............... | 514/2 |
| 7,049,283 | B2 | * | 5/2006 | Ault et al. | ............... | 514/2 |
| 7,318,925 | B2 | * | 1/2008 | Roskos et al. | ............... | 424/145.1 |
| 2006/0217313 | A1 | | 9/2006 | Azriz et al. | ............... | 514/12 |

FOREIGN PATENT DOCUMENTS

| EP | 1 397 156 | 3/2007 |
| WO | 87 00750 | 2/1987 |
| WO | 92/19262 | 11/1992 |
| WO | 96/30036 | 10/1996 |
| WO | WO 9702834 | 1/1997 |
| WO | 98 30590 | 7/1998 |
| WO | 98/34632 | 8/1998 |
| WO | 98/57656 | 12/1998 |
| WO | 00 59863 | 10/2000 |
| WO | WO-00/59563 | * 10/2000 |
| WO | 01/32201 | 5/2001 |
| WO | 02/098453 | 12/2002 |

OTHER PUBLICATIONS

Osterloh (Observations on the Effect of Parathyroid Hormone on Environmental Blood Lead Concentrations in Humans, Environmental Research 54, 8-16, 1991).*
Hodsman, L, et al, "A randomized controlled trial to compare the efficacy of cyclical parathyroid hormone versus cyclical parathyroid hormone and sequential calcitonin to improve bone mass in post menopausal women with osteoporosis", J. Clinical Endocrinology and Metabolism, vol. 82, No. 2, (1997).
Hesch, R. et al, "Increase of vertebral density by combination therapy with pulsatile 1-38hPTH and sequential addition of calcitonin nasal spray in osteoporotic patients", Calcified Tissue International, 44:176-180, (1989).
Duvos, C. et al, "Individual and combined effects of calciotropic hormones and growth factors on mineral metabolism in embryonic chick tibiae", In Vitro Cell. Dev. Biol. Animal, 33:473-478, (Jun. 1997).
Li, M., "Parathyroid hormone monotherapy and cotherapy with antiresporptive agents restore vertebral bone mass and strength in aged ovariectomized rats", Bone, vol. 16, No. 6, pp. 629-635, (Jun. 1995).
Reply of the patent proprietor to the notice(s) of Opposition, submitted to the European Patent Office in corresponding EP1,397,156 on Nov. 11, 2008.
Fujita Takuo "Parathyroid Hormone in the Treatment of Osteopororsis", Biodrugs, 15(11), pp. 721-728, (2001).
Hunziker, J. et al., "Mandibular Bone Formation Rates in Aged Ovariectomized Rats Treated wth Anti-Resporptive Agents Alone and in Combination with Intermittent Parathyroid Hormone", Journal of Dental Research, 79(6), pp. 1431-1438, (2000).
Watts, Nelson, B, "Therapies to Improve Bone Mineral Density and Reduce the Risk of Fracture Clinical Trial Results", Journal of Reproductive Medicine, 47(1, Suppl.), pp. 82-92, (2002).
Osterloh, Observations on the effect of PTH on environmental blood lead concentrations in humans, 1991, 54(1), 8-16.

* cited by examiner

*Primary Examiner* — Alton Pryor
(74) *Attorney, Agent, or Firm* — David R. Kurlandsky

(57) ABSTRACT

A method for orally administering a parathyroid hormone, PTH, comprising orally co-administering to a patient in need of PTH an effective amount of a PTH and an effective amount of calcitonin. The method according to the invention allows for the oral administration of PTH without the hypercalcemia, hypercalcuria and nephrolithiasis side effects.

13 Claims, No Drawings

ORALLY ADMINISTERING PARATHYROID HORMONE AND CALCITONIN

This is a continuation of application Ser. No. 10/478,631 filed on May 12, 2004, which is National Stage of International Application No. PCT/EP02/06017 filed on May 31, 2002, which claims benefit of provisional Application 60/295,169 filed on Jun. 1, 2001, the entire disclosures of which are hereby incorporated by reference.

BACKGROUND OF THE INVENTION

1. Field of the Invention

The present invention relates to the oral delivery of parathyroid hormone (PTH). More particularly, the invention is directed to the use of calcitonin in combination with PTH for the oral administration of PTH.

2. Description of the Related Art

PTH studies done in animals and humans with PTH, PTH-related peptides, and PTH analogs have demonstrated its usefulness in increasing bone formation and bone resorption and have prompted interest in its use for the treatment of osteoporosis and related bone disorders. However, the clinical utility of PTH is limited by the occurrence of hypercalcemia, hypercalcuria and nephrolithiasis. The occurrence of these potentially toxic side effects and alterations in calcium metabolism have remained an obstacle to exploiting the benefits of higher dosages of PTH and have required, for safety concerns, that plasma concentrations of the PTH remain within a narrow band. If the hypercalcemic effects, largely mediated by osteoclasts, could be separated from the bone formative effects, largely mediated by osteoblasts, then the therapeutic window for oral PTH therapy could be increased. In contrast to PTH, calcitonins reduce serum calcium concentrations by interacting directly with osteoclasts resulting in reduction in the bone resorptive surface area by osteoclasts and reduction in net bone resorption. Due to a decrease in plasma calcium concentration there is a corresponding decrease in urinary calcium concentrations, a known risk factor for nephrolithiasis. The present invention describes a method for orally administering PTH which broadens the therapeutic window for PTH administration and allows for the oral administration of greater PTH dosages without the potentially toxic hypercalcemic side effects.

SUMMARY OF THE INVENTION

Accordingly, the present invention is directed to a method for orally administering an effective dose of PTH comprising orally co-administering to a patient in need of PTH an effective amount of a PTH and an effective amount of a calcitonin.

Administration of PTH to primates results in increased plasma concentrations of serum parathyroid hormone and serum calcium. Conversely the administration of salmon calcitonin (sCT) to primates results is an increase in serum sCT concentrations and a reduction in serum calcium. It has now been found that the oral administration of a combination of PTH and calcitonin, while resulting in similar PTH and calcitonin plasma concentration levels as those attained upon administrations of each agent alone; quite surprisingly results in reduction of serum calcium concentrations to the level observed with calcitonin alone. In effect, the calcitonin negates the hypercalcemic effect of the PTH while attaining the same reduction in serum calcium obtained when calcitonin is administered alone, in the absence of PTH. Administering calcitonin with PTH therapy allows the additional therapeutic effects of the presently precluded PTH doses without the hypercalcemic side effects. Additionally, the calcitonin provides an analgesic effect which is useful in offsetting the bone pain usually associated with administration of PTH.

The invention is also directed to a method of stimulating new bone formation comprising orally administering to a patient in need of new bone formation a therapeutically effective amount of a PTH and a therapeutically effective amount of a calcitonin.

In a further embodiment, the invention is directed to a method of treatment or prevention of osteoporosis comprising orally administering to a patient in need of said treatment or prevention a therapeutically effective amount of a PTH and a therapeutically effective amount of a calcitonin.

The invention is also directed to a composition suitable for oral delivery comprising a PTH and a calcitonin, e.g. for simultaneous, concurrent or sequential administration of the PTH and calcitonin.

The invention is further directed to use of PTH and calcitonin for the preparation of an orally administrable medicament for the stimulation of new bone formation, e.g. for simultaneous, concurrent or sequential oral administration of the PTH and calcitonin.

The invention is yet further directed to a kit for the stimulation of new bone formation comprising PTH and calcitonin suitable for oral administration together with instructions for the oral administration thereof, e.g. for simultaneous, concurrent or sequential oral administration of the PTH and calcitonin.

Further features and advantages of the invention will become apparent from the following detailed description of the invention.

DETAILED DESCRIPTION OF THE INVENTION

The parathyroid hormone or PTH can be the full length, 84 amino acid form of parathyroid hormone, e.g. the human form, hPTH (1-84), or any polypeptide, protein, protein fragment, or modified fragment, i.e. PTH-related peptides and PTH analogs, capable of mimicking the activity of hPTH (1-84) in controlling calcium and phosphate metabolism to build bone in the human body. The PTH fragments will generally incorporate at least the first 28 N-terminal residue and include PTH (1-28), PTH (1-31), PTH (1-34), PTH (1-37), PTH (1-38) and PTH (1-41) or analogues thereof, e.g. PTS893. The PTH can be a single PTH or any combination of two or more PTHs. These parathyroid hormones are commercially available or can be obtained recombinantly, by peptide synthesis, or by extraction from human fluid by methods well established in the art.

The calcitonin for use in the instant invention can be any calcitonin, including natural, synthetic or recombinant sources thereof, as well as calcitonin derivatives such as 1,7-Asn-eel calcitonin. Various calcitonins, including salmon, pig and eel calcitonin are commercially available and commonly employed for the treatment of e.g. Paget's disease, hypercalcemia of malignancy and osteoporosis. The calcitonin can comprise a single calcitonin or any combination of two or more calcitonins. The preferred calcitonin is synthetic salmon calcitonin.

The calcitonins are commercially available or may be obtained by known methods.

The amount of PTH to be administered is generally an amount effective to stimulate new bone formation i.e. a therapeutically effective amount. This amount will necessarily vary with the age, size, sex and condition of the subject to be treated, the nature and severity of the disorder to be treated and the like. However, the amount can be less than that amount when a plurality of the compositions are to be administered, i.e., the total effective amount can be administered in cumulative dosage units. The amount of PTH can also be more than the effective amount when the composition provides sustained release of the pharmacologically active agent. The total amount of PTH to be used can be determined by methods known to those skilled in the art. However, in general, satisfactory results will be obtained systemically at daily dosages of from about 0.001 µg/kg to about 10 mg/kg animal body weight, preferably 1 µg/kg to about 6 µg/kg body weight.

The appropriate dosage of calcitonin to be administered will, of course, vary depending upon, for example, the amount of PTH to be administered and the severity of the condition being treated. However, in general, satisfactory results will be obtained systemically at daily dosages of from about 0.5 µg/kg to about 10 µg/kg animal body weight, preferably 1 µg/kg to about 6 µg/kg body weight.

The oral administration can be accomplished regularly, e.g. once or more on a daily or weekly basis; intermittently, e.g. irregularly during a day or week; or cyclically, e.g. regularly for a period of days or weeks followed by a period without administration.

The co-administration of PTH and calcitonin includes simultaneous, concurrent, or sequential administration of the two compounds. Simultaneous administration means administration of the two compounds in a single dosage form; concurrent administration means administration of the two compounds at about the same time but in separate dosage forms; and, sequential administration means administration of one of the compounds, after which the other is administered. Sequential administration may also take the form of simultaneous or concurrent administration of the two compounds, followed by cessation of the simultaneous or concurrent administration and then continued administration of one of the two compounds alone.

The oral administration of the PTH and calcitonin according to the instant invention can be accomplished in any known manner, e.g. as a liquid or solid dosage forms.

The liquid dosage forms include solution emulsions, suspensions, syrups and elixirs. In addition to the PTH and/or calcitonin, the liquid formulations may also include inert excipients commonly used in the art such as, solubilizing agents such as ethanol; oils such as cottonseed, castor and sesame oils; wetting agents; emulsifying agents; suspending agents; sweeteners; flavorings; and solvent such as water.

The solid dosage forms include capsules, soft-gel capsules, tablets, caplets, powders, granules or other solid oral dosage forms, all of which can be prepared by methods well known in the art. In addition to the PTH and/or calcitonin, these solid dosage forms generally include a pharmaceutically acceptable delivery agent for the PTH and/or calcitonin.

Suitable delivery agents are any one of the 123 modified amino acids disclosed in U.S. Pat. No. 5,866,536 or any one of the 193 modified amino acids described in U.S. Pat. No. 5,773,647 or any combination thereof. The contents of the aforementioned U.S. Pat. Nos. 5,773,647 and 5,866,536 are hereby incorporated by reference in their entirety. In addition, the delivery agent can be the disodium salt of any of the aforementioned modified amino acids as well as ethanol solvates and hydrates thereof. Suitable compounds include compounds of the following formula I

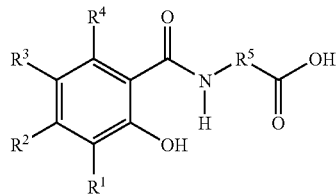

Formula I wherein $R^1$, $R^2$, $R^3$, and $R^4$ are independently hydrogen, —OH, —$NR^6R^7$, halogen, $C_1$-$C_4$alkyl, or $C_1$-$C_4$alkoxy;

$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and $R^6$ and $R^7$ are independently hydrogen, oxygen, or $C_1$-$C_4$ alkyl; and hydrates and alcohol solvates thereof. The compounds of formula I as well as their disodium salts and alcohol solvates and hydrates thereof are described in WO 00/059863, along with methods for preparing them.

The preferred delivery agents are N-(5-chlorosalicyloyl)-8-aminocaprylic acid (5-CNAC), N-(10-[2-hydroxybenzoyl] amino)decanoic acid (SNAD), N-(8-[2-hydroxybenzoyl] amino)caprylic acid (SNAC) and their monosodium and disodium salts, ethanol solvates of their sodium salts and the monohydrates of their sodium salts and any combinations thereof. The most preferred delivery agent is the disodium salt of 5-CNAC and the monohydrate thereof.

The pharmaceutical compositions of the present invention typically contain a delivery effective amount of one or more of the delivery agents, i.e. an amount sufficient to deliver the PTH and/or calcitonin for the desired effect. Generally, the delivery agent is present in an amount of 2.5% to 99.4% by weight, more preferably 25% to 50% by weight of the total composition.

The compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102 supplied by FMC corporation, or any combination thereof. Other additives may include phosphate buffer salts, citric acid, glycols, and other dispersing agents.

The composition may also include one or more enzyme inhibitors, such as actinonin or epiactinonin and derivatives thereof; aprotinin, Trasylol and Bowman-Birk inhibitor.

Further, a transport inhibitor, i.e. a ρ-glycoprotein such as Ketoprofin, may be present in the compositions of the present invention.

The solid pharmaceutical compositions of the instant invention can be prepared by conventional methods e.g. by blending a mixture of the active agent or active agents, the delivery agent, and any other ingredients, kneading, and filling into capsules or, instead of filling into capsules, molding followed by further tableting or compression-molding to give tablets. In addition, a solid dispersion may be formed by known methods followed by further processing to form a tablet or capsule.

Preferably, the ingredients in the pharmaceutical compositions of the instant invention are homogeneously or uniformly mixed throughout the solid dosage form.

The oral administration of the present invention may be to any animal in need thereof, including, but not limited to, mammals, such as rodents, cows, pigs, dogs, cats, and primates, particularly humans.

The following examples serve to further illustrate the invention.

Example 1

The following capsules are prepared as follows:
Capsules prepared from 400 mg 5-CNAC disodium salt/800 mcg sCT/800 mcg PTH (Capsule 1A)
Capsules prepared from 400 mg 5-CNAC disodium salt/800 mcg PTH (Capsule 1B)
Capsules prepared from 400 mg 5-CNAC disodium salt/800 mcg sCT (Capsule 1C)
Capsules prepared from 800 mcg PTH (Capsule 1D)

The PTH is PTH fragment 1-34, commercially available. The sCT is salmon calcitonin. The capsules are all prepared as dry blends by weighing out the individual components blending them together to make a homogeneous mix and then hand filling 400 mg of the mix into each capsule. For the PTH only capsules, the PTH is weighed out and 400 mg placed directly into each capsule.

Example 2

Primate Administration

The capsules prepared in Example 1 are administered to Rhesus monkeys as follows: four monkeys in a group are each dosed with one capsule prepared as in Example 1 as follows:

The Rhesus monkeys fast overnight prior to dosing and are restrained in chairs fully conscious, for the duration of the study period. The capsules are administered via a gavage tube followed by 10 mL of water.

Blood samples are collected at 0, 0.25, 0.5, 0.75, 1, 1.5, 2, 3, 4, 5, and 6 hours after administration. Plasma salmon calcitonin and plasma PTH are determined by radioimmunoassay. The primate plasma salmon calcitonin (sCT) and PTH results from each group of monkeys are averaged and the maximum mean plasma calcitonin are calculated and reported in Tables 1-5

TABLE 1

SALMON CALCITONIN and PTH
SCT PLASMA CONCENTRATIONS (pg/mL) AFTER
ORAL ADMINISTRATION TO THE RHESUS MONKEY
Dose: 1 Capsule 1A

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| S961 | 0 | 27 | 39 | 54 | 49 | 39 | 26 | 12 | 0 | 0 | 0 |
| S983 | 0 | 386 | 747 | 628 | 774 | 802 | 811 | 305 | 174 | 36 | 0 |
| S985 | 0 | 470 | 502 | 603 | 648 | 634 | 521 | 204 | 73 | 40 | 32 |
| E56 | 0 | 251 | 270 | 273 | 246 | 171 | 124 | 49 | 19 | 0 | 11 |
| Mean | 0 | 284 | 389 | 389 | 429 | 411 | 370 | 143 | 66 | 19 | 11 |
| SD | 0 | 194 | 304 | 276 | 339 | 365 | 364 | 137 | 78 | 22 | 15 |
| SEM | 0 | 97 | 152 | 138 | 170 | 182 | 182 | 68 | 39 | 11 | 8 |

LLOQ = 11 pg/mL, concentrations below LLOQ were set to zero.

TABLE 2

SALMON CALCITONIN and PTH
PTH PLASMA CONCENTRATIONS (pg/mL) AFTER
ORAL ADMINISTRATION TO THE RHESUS MONKEY
Dose: 1 Capsule 1A

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| S961 | 0 | 0 | 0 | 26 | 27 | 28 | 0 | 0 | 0 | 0 | 0 |
| S983 | 0 | 175 | 309 | 181 | 202 | 226 | 213 | 75 | 34 | 0 | 0 |
| S985 | 0 | 133 | 206 | 261 | 299 | 252 | 175 | 75 | 29 | 0 | 0 |
| E56 | 0 | 89 | 124 | 158 | 144 | 105 | 90 | 61 | 35 | 28 | 0 |
| Mean | 0 | 99 | 160 | 156 | 168 | 153 | 119 | 53 | 25 | 7 | 0 |
| SD | 0 | 75 | 131 | 98 | 113 | 105 | 95 | 36 | 17 | 14 | 0 |
| SEM | 0 | 37 | 65 | 49 | 57 | 52 | 47 | 18 | 8 | 7 | 0 |

LLOQ = 25 pg/mL, concentrations below LLOQ were set to zero.

TABLE 3

SALMON CALCITONIN
CALCIUM PLASMA CONCENTRATIONS (pg/mL) AFTER
ORAL ADMINISTRATION TO THE RHESUS MONKEY
Dose: 1 Capsule 1C

| Animal no. | Time [hours] | | | | | | |
|---|---|---|---|---|---|---|---|
| | 0 | 1 | 2 | 3 | 4 | 5 | 6 |
| R944 | 0.00 | −3.08 | −6.54 | −8.99 | −13.89 | −12.88 | −13.75 |
| S966 | 0.00 | −9.74 | −17.30 | −23.43 | −24.86 | −31.27 | −30.70 |
| S945 | 0.00 | −2.36 | −2.81 | −7.24 | −9.75 | −11.23 | −11.96 |
| S961 | 0.00 | −7.00 | −12.92 | −13.06 | −18.69 | −18.27 | −23.91 |
| GP943 | 0.00 | −1.54 | −7.97 | −10.36 | −17.23 | −13.50 | −12.60 |
| S9510 | 0.00 | −9.16 | −12.05 | −15.07 | −20.16 | −22.49 | −26.07 |
| Mean | 0.00 | −5.48 | −9.93 | −13.02 | −17.43 | −18.27 | −19.83 |
| SD | 0.00 | 3.61 | 5.17 | 5.82 | 5.21 | 7.59 | 8.06 |
| SEM | 0.00 | 1.47 | 2.11 | 2.38 | 2.13 | 3.10 | 3.29 |

TABLE 4

PTH
PTH PLASMA CONCENTRATIONS (pg/mL) AFTER
ORAL ADMINISTRATION TO THE RHESUS MONKEY
Dose: 1 Capsule 1B

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| R944 | 0 | 83 | 191 | 300 | 360 | 262 | 154 | 35 | 0 | 0 | 0 |
| S963 | 0 | 127 | 332 | 663 | 1258 | 150 | 34 | 0 | 0 | 0 | 0 |
| Mean | 0 | 105 | 262 | 482 | 809 | 206 | 94 | 17 | 0 | 0 | 0 |
| SD | 0 | 31 | 100 | 257 | 635 | 79 | 85 | 25 | 0 | 0 | 0 |
| SEM | 0 | 22 | 71 | 182 | 449 | 56 | 60 | 17 | 0 | 0 | 0 |

TABLE 5

PTH
PTH PLASMA CONCENTRATIONS (pg/mL) AFTER
ORAL ADMINISTRATION TO THE RHESUS MONKEY
Dose: 1 Capsule 1D

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| R927 | 0 | 0 | 0 | 0 | 0 | 0 | 0 | 0 | 0 | 0 | 0 |
| S982 | 0 | 0 | 0 | 0 | 0 | 0 | 0 | 0 | 0 | 0 | 0 |
| Mean | 0 | 0 | 0 | 0 | 0 | 0 | 0 | 0 | 0 | 0 | 0 |
| SD | 0 | 0 | 0 | 0 | 0 | 0 | 0 | 0 | 0 | 0 | 0 |
| SEM | 0 | 0 | 0 | 0 | 0 | 0 | 0 | 0 | 0 | 0 | 0 |

TABLE 5-continued

PTH
PTH PLASMA CONCENTRATIONS (pg/mL) AFTER
ORAL ADMINISTRATION TO THE RHESUS MONKEY
Dose: 1 Capsule 1D

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |

LLOQ = 25 pg/mL, concentrations below LLOQ were set to zero.

As can be seen from the data in Tables 1-5, the sCT and PTH plasma levels are essentially the same whether the compounds are administered separately or together. However, the oral administration of a combination of PTH and calcitonin, while resulting in similar PTH and calcitonin plasma concentration levels as those attained upon administrations of each agent alone; quite surprisingly results in reduction of serum calcium concentrations to the level observed with calcitonin alone.

The foregoing embodiments and examples are given merely to illustrate the instant invention and are not intended to be limiting. Numerous other embodiments and variations are within the scope of the invention and readily accessible to those skilled in the art.

We claim:

1. A pharmaceutical composition for oral administration comprising a parathyroid harmone (PTH), a calcitonin and a salmon delivery agent selected from the group consisting of N-(5-chlorosalicyloyl)-8-aminocaprylic acid (5-CNAC), N-(10-[2-hydroxybenzoly]amino)decanoic acid (SNAD), N-(8-[2-hydroxybenzoyl]amino)caprylic acid (SNAC) and pharmaceutically acceptable salts thereof.

2. The pharmaceutical composition of claim 1, wherein the PTH is a human form of PTH.

3. The pharmaceutical composition of claim 2, wherein the human form of PTH is the human PTH 1-34.

4. The pharmaceutical composition of claim 1, wherein the delivery agent is 5-CNAC or the disodium salt of 5-CNAC.

5. A method for the stimulation of bone formation comprising orally administering to a patient in need thereof a therapeutically effective amount of the composition of claim 1.

6. The method of claim 5, wherein the PTH is a human form of PTH.

7. The method of claim 6, wherein the human form of PTH is the human PTH 1-34.

8. The method of claim 5, wherein the delivery agent is 5-CNAC or the disodium salt of 5-CNAC.

9. A method for the treatment of osteoporosis comprising orally administering to a patient in need thereof a therapeutically effective amount of the composition of claim 1.

10. The method of claim 9, wherein the PTH is a human form of PTH.

11. The method of claim 10, wherein the human form of PTH is the human PTH 1-34.

12. The method of claim 9, wherein the delivery agent is 5-CNAC or the disodium salt of 5-CNAC.

13. A method for treating hypercalcemia in a patient receiving PTH comprising orally administering to a patient in need thereof a therapeutically effective amount of the composition of claim 1.

* * * * *